(12) United States Patent
Hanks

(10) Patent No.: US 11,845,903 B2
(45) Date of Patent: Dec. 19, 2023

(54) HIGH YIELD JET FUEL AND CHEMICALS FROM OZONOLYSIS OF TRIGLYCERIDES

(71) Applicant: ExxonMobil Technology and Engineering Company, Annandale, NJ (US)

(72) Inventor: Patrick L. Hanks, Bridgewater, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 0 days.

(21) Appl. No.: 17/930,468

(22) Filed: Sep. 8, 2022

(65) Prior Publication Data

US 2023/0136255 A1 May 4, 2023

Related U.S. Application Data

(60) Provisional application No. 63/263,397, filed on Nov. 2, 2021.

(51) Int. Cl.
| | | |
|---|---|---|
| *C10G 69/02* | (2006.01) | |
| *C07D 323/02* | (2006.01) | |
| *C07C 51/34* | (2006.01) | |
| *C10G 3/00* | (2006.01) | |
| *C11C 1/04* | (2006.01) | |
| *B01J 10/00* | (2006.01) | |

(Continued)

(52) U.S. Cl.
CPC ............. *C10G 69/02* (2013.01); *B01D 3/14* (2013.01); *B01J 10/00* (2013.01); *B01J 19/245* (2013.01); *C07C 1/20* (2013.01); *C07C 1/207* (2013.01); *C07C 1/22* (2013.01); *C07C 1/24* (2013.01); *C07C 51/34* (2013.01); *C07D 323/02* (2013.01); *C10G 3/50* (2013.01); *C11C 1/04* (2013.01); *B01J 2219/0004* (2013.01); *C10G 2300/1011* (2013.01); *C10G 2400/08* (2013.01)

(58) Field of Classification Search
CPC .. C10G 69/02; C10G 3/50; C10G 2300/1011; C10G 2400/08; B01D 3/14; B01J 10/00; B01J 19/245; B01J 2219/0004; C07C 1/20; C07C 1/207; C07C 1/22; C07C 1/24; C07C 51/34; C07D 323/02; C11C 1/04
See application file for complete search history.

(56) References Cited

U.S. PATENT DOCUMENTS

| | | | |
|---|---|---|---|
| 2011/0196114 A1* | 8/2011 | Le | C08L 23/02 526/75 |
| 2011/0230687 A1* | 9/2011 | Luetkens, Jr. | C10L 1/04 585/14 |

(Continued)

*Primary Examiner* — Ali Z Fadhel
(74) *Attorney, Agent, or Firm* — Shook, Hardy & Bacon L.L.P.

(57) ABSTRACT

A method for producing jet range hydrocarbons may include reacting at least a portion a fatty acid stream comprising C18:1 free fatty acid with ozone in an ozonolysis unit to form at least a C18:1 ozonide intermediate; introducing the C18:1 ozonide intermediate into a reactor, wherein at least a portion of the C18:1 ozonide intermediate is reacted with a reductive agent to produce oxidized products comprising azelaic acid and nonanoic acid; and introducing the oxidized products into a hydrotreating unit, wherein at least a portion of the oxidized products is hydrotreated to produce a paraffin product comprising nonane.

17 Claims, 2 Drawing Sheets

(51) Int. Cl.
*B01D 3/14* (2006.01)
*B01J 19/24* (2006.01)
*C07C 1/20* (2006.01)
*C07C 1/207* (2006.01)
*C07C 1/24* (2006.01)
*C07C 1/22* (2006.01)

(56) References Cited

U.S. PATENT DOCUMENTS

| | | | |
|---|---|---|---|
| 2014/0031584 A1* | 1/2014 | Foley | C07C 51/373 |
| | | | 562/512 |
| 2015/0005520 A1* | 1/2015 | Benecke | C07C 69/003 |
| | | | 554/1 |
| 2015/0018260 A1* | 1/2015 | Benecke | C11C 3/02 |
| | | | 560/204 |
| 2015/0080599 A1* | 3/2015 | Garbark | C11C 3/006 |
| | | | 560/182 |
| 2015/0087850 A1* | 3/2015 | Benecke | C07C 67/00 |
| | | | 554/168 |

* cited by examiner

HIGH YIELD JET FUEL AND CHEMICALS FROM OZONOLYSIS OF TRIGLYCERIDES

CROSS-REFERENCE TO RELATED APPLICATIONS

This application claims the benefit of U.S. Provisional Application No. 63/263,397, filed on Nov. 2, 2021, the entire contents of which are incorporated herein by reference.

FIELD

This application relates to processes and systems that utilize ozonolysis of triglycerides to produce jet fuel such as hydrocarbons with carbons numbers from C9 to C16.

BACKGROUND

Aviation is difficult to decarbonize due to the need for energy dense fuel sources. Conventional jet fuels are advantageous as they are readily produced from fractional distillation of crude oil, have high energy density, and are liquid across a broad range of temperatures and pressures. The hydrocarbons in jet fuel are typically mixtures of paraffin, naphthene, and aromatics with carbon numbers from 9 to 16 (C9-C16). Jet fuels are typically formulated with various ratios of isomers of the C9-C16 hydrocarbons to provide the desired cold pour properties, freezing point, density, autoignition temperature, and other physical properties.

While there has been strong interest in the industry to produce a bio-jet fuel derived partially or entirely from renewable resources, there are few natural sources of fatty acid chains that can be used to produce jet fuel within the acceptable C9-C16 carbon range. Commercially available fats and oils are relatively expensive starting materials and any inefficiencies in the process which reduce yield are to the detriment of the cost of the final product jet fuel. Soybean or canola oils, for example, have carbon chain lengths from C16 to C18, which can be hydrocracked to produce jet fuels. The hydrocracking process produces significant quantities of light ends paraffinic naphtha, thereby reducing the overall yield of jet fuel.

SUMMARY

Disclosed herein are example processes and systems that utilize ozonolysis of triglycerides to produce jet fuel such as hydrocarbons with carbons numbers from C9 to C16. A method for producing jet range hydrocarbons may include: reacting at least a portion a fatty acid stream comprising C18:1 free fatty acid with ozone in an ozonolysis unit to form at least a C18:1 ozonide intermediate; introducing the C18:1 ozonide intermediate into a reactor, wherein at least a portion of the C18:1 ozonide intermediate is reacted with a reductive agent to produce oxidized products comprising azelaic acid and nonanoic acid; and introducing the oxidized products into a hydrotreating unit, wherein at least a portion of the oxidized products is hydrotreated to produce a paraffin product comprising nonane.

Further disclosed herein is a method for producing jet range hydrocarbons including: hydrolyzing a triglyceride stream to produce a fatty acid stream comprising free fatty acid, introducing the fatty acid stream into an ozonolysis reactor, wherein at least a portion of the free fatty acid is reacted with ozone to produce at least an ozonide intermediate; reacting the ozonide intermediate with an oxidative agent or a reductive agent to produce oxidized products corresponding to the free fatty acid; introducing the oxidized products into a hydrotreating unit, wherein at least a portion of the oxidized products are hydrotreated to produce a paraffin stream comprising paraffins corresponding to the oxidized products; and introducing the paraffin stream into an isomerization unit wherein at least a portion of the paraffin product is isomerized to produce a corresponding iso-paraffin.

Further disclosed herein is system for producing jet range hydrocarbons including: an ozonolysis unit fluidically coupled to a free fatty acid stream comprising free fatty acid, wherein the ozonolysis unit is configured to react at least a portion of the free fatty acid stream with ozone to produce at least an ozonide intermediate corresponding to the free fatty acid in the fatty acid stream and wherein the ozonolysis unit is configured to react at least a portion of the ozonide intermediate with an oxidative agent to produce at least an oxidized product stream comprising oxidized products corresponding to the ozonide intermediate; a hydrotreating unit fluidically coupled to the oxidized product stream, wherein the hydrotreating unit is configured to react at least a portion of the oxidized products with hydrogen to produce at least a paraffin product stream comprising paraffins corresponding to the oxidized products; and an isomerization unit fluidically coupled to the paraffin product stream, wherein the isomerization unit is configured to isomerize at least a portion of the paraffins to produce an isomerized product stream comprising iso-paraffins.

These and other features and attributes of the disclosed example processes and systems that utilize ozonolysis of triglycerides to produce jet fuel such as hydrocarbons with carbons numbers from C9 to C16 of the present disclosure and their advantageous applications and/or uses will be apparent from the detailed description which follows.

BRIEF DESCRIPTION OF THE DRAWINGS

To assist those of ordinary skill in the relevant art in making and using the subject matter hereof, reference is made to the appended drawings, wherein.

DETAILED DESCRIPTION

Figure 1:
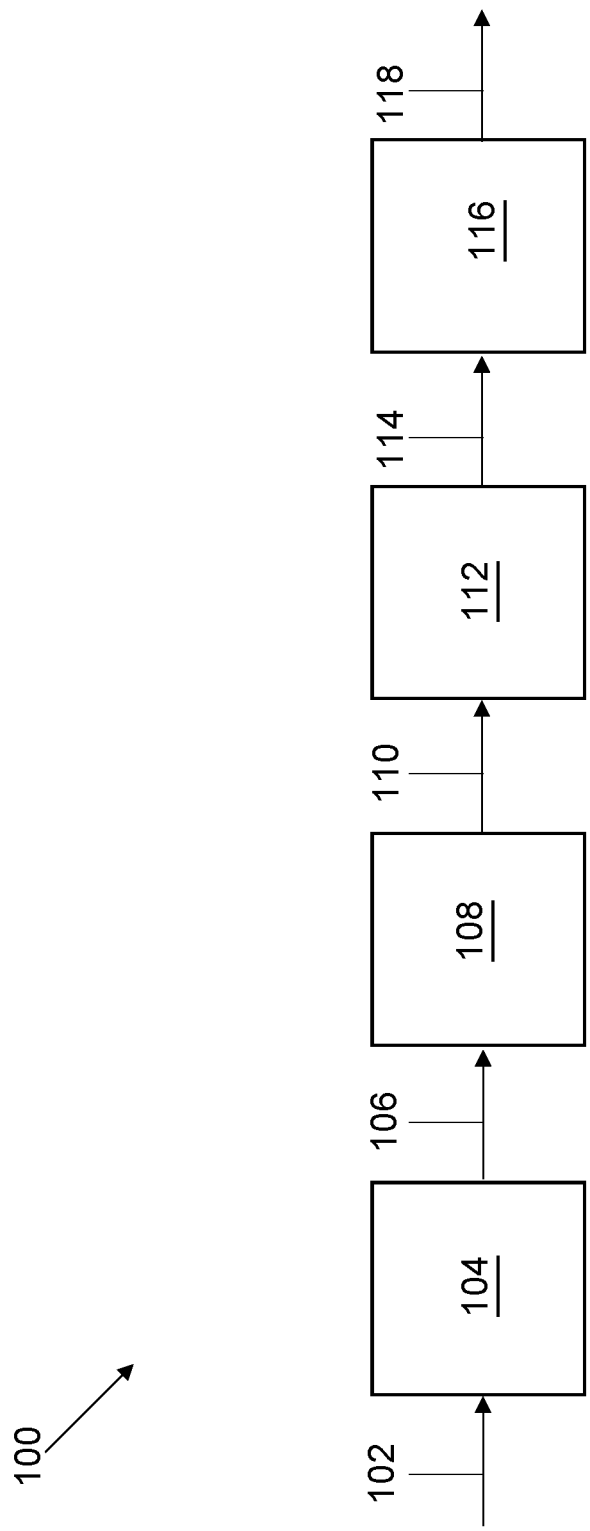
FIG. 1 is a block flow diagram of an embodiment of a process for producing jet range hydrocarbons from triglycerides.

The following is a detailed description of the disclosure provided to aid those skilled in the art in practicing the present disclosure. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description of the disclosure herein is for describing particular embodiments only and is not intended to be limiting of the disclosure.

This application relates to methods and systems for producing jet range hydrocarbons from triglycerides sourced from natural sources. In example embodiments, jet range hydrocarbons include paraffins, naphthenes, and aromatics with carbon numbers from 9 to 16 (C9-C16) and isomers thereof. The process described herein is versatile and example embodiments are suitable for producing jet range hydrocarbons from many different grades and sources of triglycerides. Further, the example embodiments of the process described herein are selective to jet range hydrocarbons which result in increased yield as compared to hydrocracking or other processes for producing jet range hydrocarbons from triglycerides. The example processes described herein include several unit operations including hydrolysis of the triglycerides to produce fatty acids and ozonolysis of the fatty acids to produce the jet range hydrocarbons. While the processes described herein may be suitable for use for a variety of triglycerides, example embodiments of the process are particularly suited for triglycerides which produce fatty acids where the carbon chain is 18 carbons long with the double bond on the $9^{th}$ carbon, sometimes referred to as C 18:1.

There may be several potential advantages to the methods and systems disclosed herein, only some of which may be alluded to in the present disclosure. As discussed above, current techniques for producing jet range hydrocarbons from triglycerides may be problematic due to the relatively high cost of materials and production of products which fall outside the acceptable carbon number range of jet fuel. The ozonolysis reaction described herein provides a scalable process with improved kinetics and selectivity to jet range hydrocarbons without the typical problems associated with low jet range hydrocarbon yield from hydrocracking.

Embodiments of the methods and systems described herein include triglyceride as a starting material. Examples of suitable triglycerides include any triglyceride which includes at least one unsaturated fatty acid molecule with a carbon chain length of at least C18 to C32 and at least one unsaturated bond on at least the $9^{th}$ carbon or greater. Any symmetrical or unsymmetrical triglyceride which meets these constraints may be used in the present process. While in principle, any triglyceride with any degree of unsaturation may be utilized, each degree of unsaturation of the fatty acid will result in a separate hydrocarbon molecule in the ozonolysis reaction thereby potentially reducing the yield to jet range hydrocarbons as hydrocarbons outside of the C9-C16 range may be produced. As such, at least a portion of the triglyceride should contain at least one fatty acid with a carbon number from C18-C32 and a single degree of saturation on the 9th carbon. One example of a suitable triglyceride includes triolein which is a symmetrical triglyceride derived from glycerol and three units of oleic acid.

Example embodiments of the triglyceride include natural sources such as a seed and/or plant oils. Some example sources include, without limitation, soy oil, canola oil, camelina oil, olive oil, macadamia oil, sunflower oil, and combinations thereof. Examples of vegetable oils that can be used in accordance with this invention include, but are not limited to rapeseed (canola) oil, soybean oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, and rice bran oil. Example algal sources for algae oils include, but are not limited to, unicellular and multicellular algae. Examples of such algae include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae is of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis camerae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella*, and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, and *Xenococcus* species. Alternatively, or in addition to seed and/or plant oils, the example embodiments of the triglyceride are sourced from an algae that is capable of producing triglycerides which include at least one unsaturated fatty acid molecule with a carbon chain length of at least C18 to C32 and at least one unsaturated bond on at least the 9th carbon or greater. The algae strain is be selected for its tendency to produce the triglyceride described above or is genetically engineered to produce triglycerides with the properties suitable for production of jet range hydrocarbons.

In some embodiments, a first step in the process includes conversion of the triglyceride to the corresponding fatty acids and glycerol by hydrolyzing the triglyceride, sometimes referred to as fat splitting. Example embodiments of the method include the continuous Colgate-Emery process, where nearly complete (>95%) hydrolysis can be achieved by operating around 200-260° C. and pressures up to 50 barg. The reaction example embodiments are carried out counter-currently with fat addition at the bottom of the tower and water is added at the top of the tower. Residence times of both phases are on the order of 2-3 hours. The hydrolysis example embodiments are performed by contacting the triglyceride with steam at conditions which convert at least a portion of the triglyceride into the corresponding fatty acids and glycerol. The hydrolysis reaction example embodiments are carried out in a hydrolysis reactor such as a batch reactor whereby steam is sparged into a batch reactor until the desired fraction of triglyceride have been converted. Alternatively, hydrolysis example embodiments are carried out continuously by counter-currently contacting the triglyceride with steam in a column-type reactor, for example, where the triglyceride os introduced into a top of the column-type reactor and steam is sparged into the bottom of the column-type reactor. The steam ascends through the column reactor and contacting the triglyceride thereby breaking the triglyceride into the corresponding fatty acids and glycerol. In example embodiments glycerol is stripped from the fatty acids by the steam and is carried out of the column-type reactor as an overheads stream while the fatty acids formed is be drawn off as a bottoms stream.

In example embodiments, steam used in the hydrolysis reaction is at any temperature and pressure suitable to hydrolyze the triglyceride without substantially polymerizing the resultant fatty acids. For example, steam at a temperature of 200° C. —260° C. and at a pressure of up to 50 barg. Conversion of the triglyceride to fatty acid is in the range of 10% to 99% depending on the residence time of the hydrolysis reactor. Hydrolysis is rate limited by kinetics such that a longer residence time generally correspond to greater conversion of the triglyceride. In some embodiments, an additional catalyst is utilized to increase reaction rate. In example embodiments after the hydrolysis step, the fatty acids and glycerol are separated, for example by stripping the glycerol from the fatty acids using steam or adding water to the glycerol/fatty acid product thereby dissolving at least a portion of the glycerol in an aqueous phase which is then be removed by separating the aqueous phase from a fatty acid phase. Alternatively, the fatty acids and glycerol are be separated by distillation to produce a fatty acid stream with reduced glycerol content.

In example embodiments the fatty acids generated during the hydrolysis step are used directly in the ozonolysis step. However, lower carbon number unsaturated fatty acids generated during the hydrolysis step may not be suitable for ozonolysis as the resultant hydrocarbons may be outside the suitable carbon numbers for jet fuel. As discussed above, the lowest carbon number typically suitable for jet fuel is C9 and as such, any fatty acids with carbon numbers less than C18 may generate hydrocarbons outside jet fuel range. In example embodiments, another step is to fractionate the fatty acids generated in the hydrolysis step before ozonolysis such that hydrocarbons generated are within the jet hydrocarbon range. In example embodiments fatty acids fractionated by distillation, for example, to generate a bottoms stream with C18 and heavier fatty acids and an overheads stream with C17 and lighter fatty acids. The C18 and heavier stream include C 18s, such as stearic acid (C18:0), oleic acid (C18:1), and linoleic acid (C18:2), for example. In some embodiments, the C18 and heavier stream may further include heavier saturated fatty acids such as arachidic acid and behenic acid, and heavier unsaturated fatty acids such as arachidonic acid, for example.

In example embodiments the C18 and heavier stream is used directly in the ozonolysis step as saturated stearic acid is mostly unreactive in ozonolysis while oleic, linoleic, alpha linoleic acid, and heavier unsaturated fatty acids undergo ozonolysis reactions. In example embodiments the C18s is fractionated further to produce a C18 cut which may be sent to ozonolysis which may include C18:1, C18:0, and C18:2, if present. In some examples, additional fractionation aids such as urea and/or methanol may be utilized during fractionation to aid in separating the fatty acids. Alternatively, or in addition for fractionation, the fatty acids may be further purified by crystallization techniques such as extractive crystallization to separate saturated fatty acids from unsaturated fatty acids.

In some embodiments, a second step in the process includes ozonolysis of the fatty acid or fractions thereof generated in the hydrolysis step. Alternatively, or in addition to fatty acids from hydrolysis, the ozonolysis step may be carried out using fatty acids from any source such as a storage tank, pipeline, or other chemical process. It should be understood that the present disclosure is non-limiting to the source of fatty acid utilized in the ozonolysis step.

In the ozonolysis step, unsaturated fatty acids such as oleic acid and linoleic acid are reacted with ozone in a solvent to produce an ozonide intermediate. In example embodiments the ozonide intermediate is further reacted under oxidative or reductive conditions to produce oxidized products such as ketones, aldehydes, alcohols, carboxylic acids, and carboxylic diacids corresponding to the fatty acids. An example of an ozonolysis reaction is shown in reaction 1 where oleic acid is reacted with ozone to produce the linoleic ozonide intermediate. In reaction 2, the linoleic ozonide intermediate is reacted under oxidative conditions to produce azelaic acid and caproic acid as the major products. Other minor products of reaction 2 may include malonic acid and hexanoic acid. The solvent used in the ozonolysis step may include any suitable solvent in which the fatty acids acre miscible such as alcohols including methanol, ethanol, propanol, methyl acetate, DMSO, dimethylformamide, ether, chloroform, hydrocarbon solvents such as C5-C12 hydrocarbons, combinations thereof. The oxidative or reductive conditions to produce the oxidized products may include any suitable reagents. Some examples of suitable oxidative agents may include, but are not limited to, hydrogen peroxide, for example. Some examples of suitable reductive agents may include, but are not limited to, triphenylphosphine, thiourea, zinc, dimethyl sulfide, sodium borohydride, hydrogen over a catalyst such as platinum or palladium, and combinations thereof.

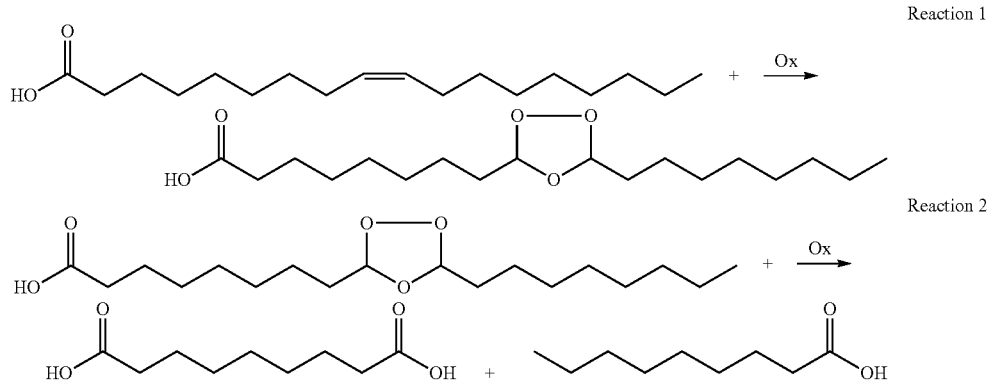

Reaction 1

Reaction 2

In example embodiments the ozonolysis step includes introducing the fatty acid, solvent, and ozone into a vessel and allowing the ozone to react with the fatty acid to form the ozonide intermediate. The vessel include any suitable gas-liquid contactor vessels for carrying out the heterogenous reaction between gaseous ozone and liquid fatty dissolved in solvent. For example, the vessel may include, without limitation a falling film column, a plate column, a packed column, a bubble column reactor, or a spray tower. The vessel may be operated at any suitable conditions for performing the ozonolysis reaction including at a temperature in a range of 20° C. to 50° C. Alternatively the ozonolysis reaction may be carried out at a temperature in a range of 20° C. to 30°, 30° C. to 40° C., 40° C. to 50° C., or any ranges therebetween. In example embodiments ozone is be added in any suitable amount, including from 1 to 5 times stoichiometric amounts relative to the number of unsaturated bonds in the fatty acid. Without being limited by theory, the extent of reaction of the ozone with fatty acid is be limited by kinetics. As such, the longer the reaction is allowed to proceed, the greater the extent of reaction tends to be. Conversion of 90% or greater by weight of the fatty acid to the ozonide intermediate may be realized by relatively longer reaction times. For example, the reaction may be carried out for a period of 10 minutes to 6 hours which may be dependent on vessel design and volume.

In some embodiments, a third step in the process includes mixing an oxidative agent or a reductive agent with the ozonide intermediate and allowing the oxidative or reductive agent to react with the ozonide intermediate to produce the oxidized products such as ketones, aldehydes, alcohols, carboxylic acids, and carboxylic diacids corresponding to the ozonide intermediate derived from the fatty acid. In embodiments where the fatty acids include oleic acid, the oxidized products include C9 oxidized products such as azelaic acid and nonanoic acid, for example. In example embodiments suitable conditions for reacting the ozonide intermediate with the oxidative agent or reductive agent may be used, including at a temperature in a range of 20° C. to 50° C. Alternatively the reaction is carried out at a temperature in a range of 20° C. to 30°, 30° C. to 40° C., 40° C. to 50° C., or any ranges therebetween. The reaction is carried out a pressure in a range of 10 kPa to 120 kPa. Alternatively at a pressure in a range of 10 kPa to 30 kPa, 30 kPa to 60 kPa, 60 kPa to 90 kPa, 90 kPa to 120 kPa, or any ranges therebetween. Without being limited by theory, the extent of reaction of the ozonide intermediate with the oxidative agent or reductive agent may be limited by kinetics. As such, the longer the reaction is allowed to proceed, the greater the extent of reaction may tend to be. Conversion of 90% or greater by weight of the ozonide intermediate may be realized by relatively longer reaction times. For example, the reaction may be carried out for a period of 10 minutes to 6 hours which may be dependent on vessel design and volume.

In some embodiments, a fourth step in the process includes hydrotreating the oxidized products in a hydrotreater unit. In the hydrotreater unit the oxidized products are reacted with hydrogen in the presence of a hydrotreater catalyst to produce the corresponding paraffins from the oxidized products. In embodiments where the oxidized products include azelaic acid and nonanoic acid, a product of hydrotreatment includes n-nonane. Hydrotreating units may utilize hydrotreating catalysts such as sulfides of Co and Mo or Ni and Mo on a support to catalyze the addition of hydrogen to a feed material. The catalyst in a hydrotreatment stage can be a conventional hydrotreating catalyst, such as a catalyst composed of a Group NIB metal and/or a Group VIII metal on a support. Suitable metals include cobalt, nickel, molybdenum, tungsten, or combinations thereof. Preferred combinations of metals include nickel and molybdenum or nickel, cobalt, and molybdenum. Suitable supports include silica, silica-alumina, alumina, and titania. The amount of Group VI metal supported on the catalyst support can vary depending on the catalyst. Suitable total amounts of metals range from 1 wt % to 35 wt % relative to the total weight of the catalyst In example embodiments, platinum or palladium without sulfur is utilized for deoxygenation and olefin saturation. Hydrotreating catalysts may be affected by the presence of oxygen in the oxidized products thereby reducing the activity of the hydrotreating catalyst. It may be advantageous to utilize a standalone hydrotreating unit, separate from other hydrotreating units in a chemical plant and/or refinery, for hydrotreating the oxidized products. Other oxidized products corresponding to unsaturated fatty acids produced in the hydrolysis reactor may be introduced into the hydrotreating unit to be converted to their corresponding paraffins. While the straight chain nonane is within the jet range hydrocarbons, nonane may not have the physical properties such as cold pour point, freezing point, density, and octane value required for jet fuel. As such, the nonane and other paraffins produced from hydrotreating may be further isomerized in an isomerization unit to produce iso-nonane with properties that align with the desired properties of jet fuel.

FIG. 1 is a block flow diagram illustrating a process 100 for producing jet range hydrocarbons from triglycerides using ozonolysis in accordance with some embodiments disclosed herein. In FIG. 1, a triglyceride stream 102 is introduced into hydrolysis unit 104. Triglyceride stream 102 may include any of the triglycerides discussed above. In hydrolysis unit 104, triglycerides from triglyceride stream 102 are reacted with steam to produce the corresponding fatty acids from the triglycerides as well as glycerol. In some embodiments the fatty acid produced includes C18:1 oleic acid. Hydrolysis unit 104 includes various different equipment for hydrolyzing the triglyceride with steam, including but not limited to, hydrolysis reactors such as hydrolysis reactor 204 on FIG. 2. For example, the hydrolysis unit 104 may include a batch reactor or a continuous reactor such as a column reactor. In some embodiments the hydrolysis unit is configured to perform the Colgate-Emery process and include the associated reactors, flash tanks, and settling tanks required.

Intermediate stream 106 containing at least a portion of the triglycerides produced in hydrolysis unit 104 is withdrawn from hydrolysis unit 104 and introduced into introduced into ozonolysis unit 108. In ozonolysis unit 108, the fatty acids from hydrolysis unit 104, or any other fatty acid source as described above, is reacted with ozone to form ozonide intermediate product corresponding to the fatty acids in intermediate stream 106. Ozonolysis unit 108 may include any of the units described above such as a bubble column, for example. The ozonide intermediate is be further reacted with an oxidative or reductive agent as discussed above to produce an oxidized products such as ketones, aldehydes, alcohols, carboxylic acids, and carboxylic diacids corresponding to the fatty acids. In example embodiments the ozonide intermediate is reacted with the oxidative or reductive agent in the same vessel as the ozonolysis reaction with the fatty acid or the ozonide intermediate may be withdrawn into a separate reactor vessel. Intermediate stream 110 containing the oxidized products is introduced into hydrotreating unit 112. Hydrotreating unit 112 may include reactors comprising hydrotreating catalysts, heaters, separators, and columns configured to perform hydrotreating operations. Hydrotreating may include a range of catalytic processes which react an input stream with hydrogen over a catalyst bed to add hydrogen to the input stream. In hydrotreating unit 112, at least a portion of the oxidized products from intermediate stream 110 is hydrotreated to produce the corresponding paraffins such as nonane. Paraffin stream 114 is withdrawn from hydrotreating unit 112 and be introduced into isomerization unit 116 where the paraffins produced in hydrotreating unit 112 is isomerized to produce iso-paraffins corresponding to the paraffins. Example embodiments isomerization unit 116 include isomerization reactors comprising an isomerization catalyst, as well as associated dryers, separation columns, pumps, and other equipment necessary to isomerize an input stream. In some embodiments the isomerization unit is be operated at 245° C. to 270° C. and 21 kg/cm$^2$ to 35 kg/cm$^2$. Product stream 118, containing the iso paraffins is withdrawn from isomerization unit 116.

Figure 2:
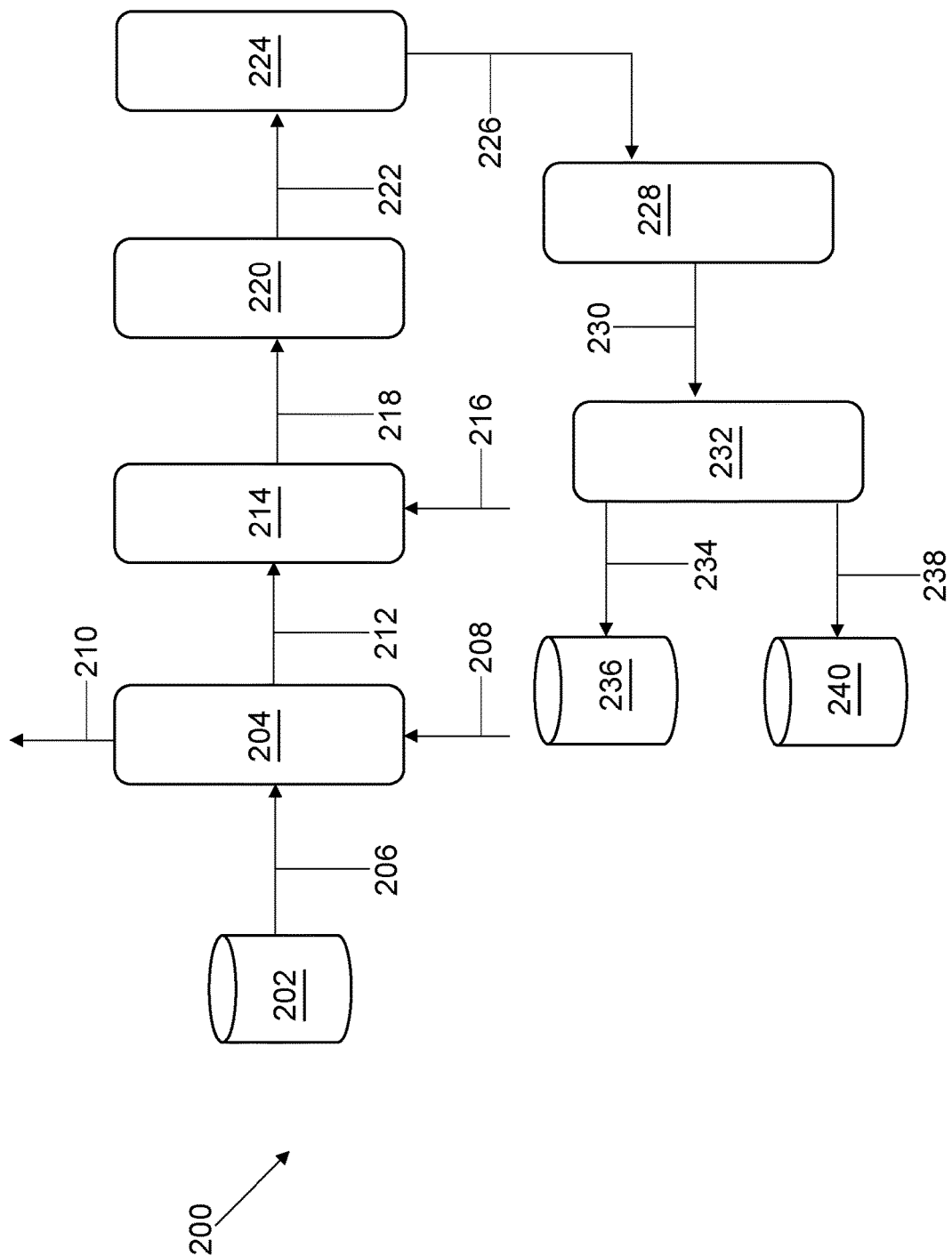
FIG. 2 is a schematic illustration of an embodiment of a process for producing jet range hydrocarbons from triglycerides.

FIG. 2 is a schematic illustration of a process 200 for producing jet range hydrocarbons from triglycerides in accordance with some embodiments disclosed herein. Process 200 may begin with triglyceride storage 202. Example embodiments of triglyceride storage 202 includes any storage system, such as a tank farm, barrels, pipeline, or any other suitable storage for the triglycerides described above. Triglycerides from triglyceride storage 202 is conveyed to hydrolysis reactor 204 through conveyance 206. Conveyance 206 include pipes, tubulars, pumps, and other equipment required to convey the triglycerides from triglyceride storage 202 to hydrolysis reactor 204.

Example embodiments of hydrolysis reactor 204 include any of the previously mentioned reactor types such as batch reactor or column-type reactor. Steam stream 208 is introduced into hydrolysis reactor 204 and is contacted with triglycerides provided from conveyance 206. The triglycerides are hydrolyzed to form the corresponding fatty acids and glycerol as described above. Hydrolysis reactor 204 is operated at any of the conditions described above. Glycerol as well as water and/or steam is withdrawn from hydrolysis reactor 204 as stream 210 and the free fatty acid is withdrawn from hydrolysis reactor 204 as stream 212. In some embodiments, additional glycerol removal may be performed such as aqueous phase absorption of the glycerol, followed by phase separation from the fatty acids. Fatty acids in stream 212 may include a range of fatty acids, the carbon number of which depends on the carbon numbers of the triglycerides which were hydrolyzed. In some embodiments, stream 212 may include fatty acids with carbon number ranging from C6 to C22, for example.

Stream 212 containing the produced fatty acids from hydrolysis reactor 204 is introduced into ozonolysis unit 214. In some embodiments stream 212 is fractionated by distillation such that the C18 cut is sent to ozonolysis unit 214. In ozonolysis unit 214, the fatty acids from stream 212 are reacted with ozone provided by ozone stream 216 to form ozonide intermediate product corresponding to the fatty acids in is stream 212. In example embodiments ozonolysis unit 214 includes any of the units described above such as a bubble column, for example. The ozonide intermedia is withdrawn from ozonolysis unit 214 and be introduced into reactor 220 where the ozonide intermediate is further reacted with an oxidative or reductive agent as discussed above to produce an oxidized products such as ketones, aldehydes, alcohols, carboxylic acids, and carboxylic diacids corresponding to the fatty acids. Oxidized product stream 222 is withdrawn from reactor 220 and introduced into hydrotreating unit 224. Hydrotreating unit 224 may include any hydrotreating units and catalysts previously described. Hydrotreating unit 224 may further include a hydrogen stream input such that the hydrotreating unit 224 may be operated at conditions suitable react at least a portion of the oxidized products with the hydrogen to produce paraffins corresponding to the oxidized products in oxidized product stream 222. Product stream 226 containing the paraffins is withdrawn from hydrotreating unit 224 and introduced into isomerization unit 228. Isomerization unit 228 may include any of the previously described isomerization units and is operated at conditions sufficient to isomerize at least a portion of the paraffins in product stream 226 to the corresponding iso-paraffins including iso-nonane in product stream 226. Isomerized stream 230 is withdrawn from isomerization unit 228 and introduced into product fractionator 232. Product fractionator 232 may include a distillation column, for example, configured to separate components of isomerized stream 230 into stream based on molecular mass. For example, product fractionator 232 may separate isomerized stream 230 into jet range hydrocarbon stream 234 comprising hydrocarbons from isomerized stream 230 with carbon numbers from 9 to 16 and diesel range hydrocarbon stream 238 comprising any other hydrocarbons from isomerized stream 230. Jet range hydrocarbon stream 234 may be send to jet mixing pool 236 while diesel range hydrocarbon stream 238 may be send to diesel mixing pool 240.

Accordingly, the preceding description describes methods and systems for producing jet range hydrocarbons from triglycerides sourced from natural sources including triglycerides. The processes and systems disclosed herein may include any of the various features disclosed herein, including one or more of the following embodiments.

Embodiment 1. A method for producing jet range hydrocarbons comprising: reacting at least a portion a fatty acid stream comprising C18:1 free fatty acid with ozone in an ozonolysis unit to form at least a C18:1 ozonide intermediate; introducing the C18:1 ozonide intermediate into a reactor, wherein at least a portion of the C18:1 ozonide intermediate is reacted with a reductive agent to produce oxidized products comprising azelaic acid and nonanoic acid; and introducing the oxidized products into a hydrotreating unit, wherein at least a portion of the oxidized products is hydrotreated to produce a paraffin product comprising nonane.

Embodiment 2. The method of embodiment 1 wherein the ozonolysis unit comprises a bubble column reactor.

Embodiment 3. The method of embodiment 1 or 2 wherein the ozone is present in an amount of from 1 to 5 times stoichiometric amount relative to a number of unsaturated bonds in the C18:1 free fatty acid.

Embodiment 4. The method of any preceding embodiment wherein the reacting at least a portion of the C18:1 free fatty acid in the fatty acid stream with ozone is carried out at a temperature in a range of from 20° C. to 50° C.

Embodiment 5. The method of any preceding embodiment further comprising introducing a solvent into the ozonolysis unit.

Embodiment 6. The method of embodiment 5 wherein the solvent comprises at least one liquid solvent selected from the group consisting of an alcohol, methyl acetate, DMSO, dimethylformamide, an ether, chloroform, a C5-C12 hydrocarbon, and combinations thereof.

Embodiment 7. The method of any preceding embodiment wherein the reductive agent comprises hydrogen over a platinum catalyst palladium catalyst, or a combination thereof.

Embodiment 8. The method of any preceding embodiment further comprising isomerizing at least a portion of the paraffin product to produce a corresponding iso-paraffin.

Embodiment 9. A method for producing jet range hydrocarbons comprising: hydrolyzing a triglyceride stream to produce a fatty acid stream comprising free fatty acid, introducing the fatty acid stream into an ozonolysis reactor, wherein at least a portion of the free fatty acid is reacted with ozone to produce at least an ozonide intermediate; reacting the ozonide intermediate with an oxidative agent or a reductive agent to produce oxidized products corresponding to the free fatty acid; introducing the oxidized products into a hydrotreating unit, wherein at least a portion of the oxidized products are hydrotreated to produce a paraffin stream comprising paraffins corresponding to the oxidized products; and introducing the paraffin stream into an isomerization unit wherein at least a portion of the paraffin product is isomerized to produce a corresponding iso-paraffin.

Embodiment 10. The method of embodiment 9, wherein the fatty acid stream comprises C18:1 fatty acid.

Embodiment 11. The method of embodiment 9 or 10 wherein the fatty acid stream further comprises at least one fatty acid selected from the group consisting of C14 fatty acid, C15 fatty acid, C16 fatty acid, C18:0 fatty acid, C18:2 fatty acid, and combinations thereof.

Embodiment 12. The method of any one of embodiments 9-11 further comprising introducing the fatty acid stream into a distillation column and separating a C18 cut comprising C18 fatty acids from the fatty acid stream, wherein the C18 cut is introduced into the ozonolysis reactor.

Embodiment 13. The method of any one of embodiments 9-12 wherein the method further comprises introducing a solvent into the ozonolysis reactor.

Embodiment 14. The method of any one of embodiments 9-13 wherein the solvent comprises at least one liquid solvent selected from the group consisting of an alcohol, methyl acetate, DMSO, dimethylformamide, an ether, chloroform, a C5-C12 hydrocarbon, and combinations thereof.

Embodiment 15. The method of any one of embodiments 9-14 wherein the oxidative agent comprises hydrogen peroxide and the reductive agent comprises at least one selected from the group consisting of triphenylphosphine, thiourea, zinc, dimethyl sulfide, sodium borohydride, hydrogen over a platinum catalyst or palladium catalyst, and combinations thereof.

Embodiment 16. A system for producing jet range hydrocarbons comprising: an ozonolysis unit fluidically coupled to a free fatty acid stream comprising free fatty acid, wherein the ozonolysis unit is configured to react at least a portion of the free fatty acid stream with ozone to produce at least an ozonide intermediate corresponding to the free fatty acid in the fatty acid stream and wherein the ozonolysis unit is configured to react at least a portion of the ozonide intermediate with an oxidative agent to produce at least an oxidized product stream comprising oxidized products corresponding to the ozonide intermediate; a hydrotreating unit fluidically coupled to the oxidized product stream, wherein the hydrotreating unit is configured to react at least a portion of the oxidized products with hydrogen to produce at least a paraffin product stream comprising paraffins corresponding to the oxidized products; and an isomerization unit fluidically coupled to the paraffin product stream, wherein the isomerization unit is configured to isomerize at least a portion of the paraffins to produce an isomerized product stream comprising iso-paraffins.

Embodiment 17. The system of embodiment 16 wherein the ozonolysis unit comprises a bubble column reactor.

Embodiment 18. The system of embodiments 15 or 16 further comprising a hydrolysis unit configured to hydrolyze at least a portion of a triglyceride stream to produce at least the free fatty acid stream.

Embodiment 19. The system of any one of embodiments 16-18 further comprising a distillation column disposed between the hydrolysis unit and the ozonolysis unit, wherein the distillation column is configured to separate a C18 cut comprising C18 fatty acids from the free fatty acid stream, wherein the C18 cut is introduced into the ozonolysis unit.

Embodiment 20. The system of any one of embodiments 16-19 further comprising a product distillation column fluidically coupled to the isomerized product stream, wherein the product distillation column is configured to separate a jet range hydrocarbon stream comprising hydrocarbons with carbon numbers from 9 to 16 from the isomerized product stream.

While the disclosure has been described with respect to a number of embodiments and examples, those skilled in the art, having benefit of this disclosure, will appreciate that other embodiments can be devised which do not depart from the scope and spirit of the disclosure as disclosed herein. Although individual embodiments are discussed, the present disclosure covers all combinations of all those embodiments.

While compositions, methods, and processes are described herein in terms of "comprising," "containing," "having," or "including" various components or steps, the compositions and methods can also "consist essentially of" or "consist of" the various components and steps. The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the disclosure, additionally, they do not exclude impurities and variances normally associated with the elements and materials used.

All numerical values within the detailed description are modified by "about" the indicated value, and take into account experimental error and variations that would be expected by a person having ordinary skill in the art.

Many alterations, modifications, and variations will be apparent to those skilled in the art in light of the foregoing description without departing from the spirit or scope of the present disclosure and that when numerical lower limits and numerical upper limits are listed herein, ranges from any lower limit to any upper limit are contemplated.

What is claimed is:

1. A method for producing jet range hydrocarbons comprising:
hydrolyzing a triglyceride stream to produce a fatty acid stream comprising free fatty acid;
introducing the fatty acid stream into a distillation column and separating a C18 and heavier cut comprising C18 fatty acids from the fatty acid stream;
reacting at least a portion the C18 and heavier cut comprising C18:1 free fatty acid with ozone in an ozonolysis unit to form at least a C18:1 ozonide intermediate;
introducing the C18:1 ozonide intermediate into a reactor, wherein at least a portion of the C18:1 ozonide intermediate is reacted with a reductive agent to produce oxidized products comprising azelaic acid and nonanoic acid; and introducing the oxidized products into a hydrotreating unit, wherein at least a portion of the oxidized products is hydrotreated to produce a paraffin product comprising nonane.

2. The method of claim 1, wherein the ozonolysis unit comprises a bubble column reactor.

3. The method of claim 1, wherein the ozone is present in an amount of from 1 to 5 times stoichiometric amount relative to a number of unsaturated bonds in the C18:1 free fatty acid.

4. The method of claim 1, wherein the reacting at least a portion of the C18:1 free fatty acid in the fatty acid stream with ozone is carried out at a temperature in a range of from 20° C. to 50° C.

5. The method of claim 1, further comprising introducing a solvent into the ozonolysis unit.

6. The method of claim 5, wherein the solvent comprises at least one liquid solvent selected from the group consisting of an alcohol, methyl acetate, DMSO, dimethylformamide, an ether, chloroform, a C5-C12 hydrocarbon, and combinations thereof.

7. The method of claim 1, wherein the reductive agent comprises hydrogen over a platinum catalyst palladium catalyst, or a combination thereof.

8. The method of claim 1, further comprising isomerizing at least a portion of the paraffin product to produce a corresponding iso-paraffin.

9. A method for producing jet range hydrocarbons comprising:

hydrolyzing a triglyceride stream to produce a fatty acid stream comprising free fatty acid, introducing the fatty acid stream into a distillation column and separating a C18 and heavier cut comprising C18 fatty acids from the fatty acid stream;

introducing the C18 and heavier cut into an ozonolysis reactor, wherein at least a portion of the free fatty acid is reacted with ozone to produce at least an ozonide intermediate;

reacting the ozonide intermediate with an oxidative agent or a reductive agent to produce oxidized products corresponding to the free fatty acid;

introducing the oxidized products into a hydrotreating unit, wherein at least a portion of the oxidized products are hydrotreated to produce a paraffin stream comprising paraffins corresponding to the oxidized products; and introducing the paraffin stream into an isomerization unit wherein at least a portion of the paraffin product is isomerized to produce a corresponding iso-paraffin.

10. The method of claim 9, wherein the fatty acid stream comprises C 18:1 fatty acid.

11. The method of claim 10, wherein the fatty acid stream further comprises at least one fatty acid selected from the group consisting of C14 fatty acid, C15 fatty acid, C16 fatty acid, C18:0 fatty acid, C18:2 fatty acid, and combinations thereof.

12. The method of claim 9, wherein the method further comprises introducing a solvent into the ozonolysis reactor.

13. The method of claim 12, wherein the solvent comprises at least one liquid solvent selected from the group consisting of an alcohol, methyl acetate, DMSO, dimethylformamide, an ether, chloroform, a C5-C12 hydrocarbon, and combinations thereof.

14. The method of claim 12, wherein the oxidative agent comprises hydrogen peroxide and the reductive agent comprises at least one selected from the group consisting of triphenylphosphine, thiourea, zinc, dimethyl sulfide, sodium borohydride, hydrogen over a platinum catalyst or palladium catalyst, and combinations thereof.

15. A system for producing jet range hydrocarbons comprising:

a hydrolysis unit configured to hydrolyze at least a portion of a triglyceride stream to produce at least a free fatty acid stream;

a distillation column disposed between the hydrolysis unit and the ozonolysis unit, wherein the distillation column is configured to separate a C18 and heavier cut comprising C18 fatty acids from the free fatty acid stream;

an ozonolysis unit fluidically coupled to the C18 and heavier cut, wherein the ozonolysis unit is configured to react at least a portion of the free fatty acid stream with ozone to produce at least an ozonide intermediate corresponding to the free fatty acid in the fatty acid stream and wherein the ozonolysis unit is configured to react at least a portion of the ozonide intermediate with an oxidative agent to produce at least an oxidized product stream comprising oxidized products corresponding to the ozonide intermediate;

a hydrotreating unit fluidically coupled to the oxidized product stream, wherein the hydrotreating unit is configured to react at least a portion of the oxidized products with hydrogen to produce at least a paraffin product stream comprising paraffins corresponding to the oxidized products; and an isomerization unit fluidically coupled to the paraffin product stream, wherein the isomerization unit is configured to isomerize at least a portion of the paraffins to produce an isomerized product stream comprising iso-paraffins.

16. The system of claim 15, wherein the ozonolysis unit comprises a bubble column reactor.

17. The system of claim 15, further comprising a product distillation column fluidically coupled to the isomerized product stream, wherein the product distillation column is configured to separate a jet range hydrocarbon stream comprising hydrocarbons with carbon numbers from 9 to 16 from the isomerized product stream.

* * * * *